(12) United States Patent
Yoshioka et al.

(10) Patent No.: US 8,164,329 B2
(45) Date of Patent: Apr. 24, 2012

(54) WIRE ROPE FLAW DETECTOR

(75) Inventors: Takashi Yoshioka, Tokyo (JP); Hiroshi Sasai, Tokyo (JP); Yoshinori Miyamoto, Tokyo (JP); Kimiyasu Furusawa, Tokyo (JP); Yukinobu Karata, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 234 days.

(21) Appl. No.: 12/524,193

(22) PCT Filed: Jan. 31, 2007

(86) PCT No.: PCT/JP2007/051560
§ 371 (c)(1),
(2), (4) Date: Jul. 23, 2009

(87) PCT Pub. No.: WO2008/093409
PCT Pub. Date: Aug. 7, 2008

(65) Prior Publication Data
US 2010/0102807 A1    Apr. 29, 2010

(51) Int. Cl.
*G01N 27/82* (2006.01)
(52) U.S. Cl. ..................... 324/240; 324/238
(58) Field of Classification Search .............. 324/240
See application file for complete search history.

(56) References Cited

U.S. PATENT DOCUMENTS 5,565,771 A    10/1996 Hamelin et al.
5,793,205 A *  8/1998 Griffith et al. ............... 324/238

FOREIGN PATENT DOCUMENTS

| GB | 2 067 766 | | 7/1981 |
| JP | 55-94156 | A | 7/1980 |
| JP | 6-087861 | U | 12/1994 |
| JP | 7-505468 | A | 6/1995 |
| JP | 9-145678 | A | 6/1997 |
| JP | 9-210968 | A | 8/1997 |
| JP | 2733088 | B2 | 12/1997 |
| JP | 11-230945 | A | 8/1999 |
| JP | 11230945 | A * | 8/1999 |

(Continued)

OTHER PUBLICATIONS

Office Action dated Dec. 20, 2010, issued in the Corresponding German Patent Application No. 11 2007 003 297.9-52, and an English Translation thereof.

(Continued)

*Primary Examiner* — Huy Q Phan
*Assistant Examiner* — Temilade S Rhodes-Vivour
(74) *Attorney, Agent, or Firm* — Buchanan Ingersoll & Rooney PC

(57) ABSTRACT

A wire rope flaw detector comprises a back yoke and excitation permanent magnets, which form a main magnetic path in a predetermined section of a wire rope in the axial direction; a magnetic path member arranged in the predetermined section to be magnetically insulated from the back yoke and the permanent magnets and making the leakage flux generated from a damaged part of wire rope detour to the outside of the wire rope; and a detection coil wound around the magnetic path member for detecting leakage flux. The amount of leakage flux can be increased by providing the magnetic path member and since the windable area of the detection coil is increased, the number of turns of detection coil can be increased.

8 Claims, 15 Drawing Sheets

FOREIGN PATENT DOCUMENTS

| | | | |
|---|---|---|---|
| JP | 2001-41933 A | | 2/2001 |
| JP | 2001108658 A | * | 4/2001 |
| JP | 2001153845 A | * | 6/2001 |
| JP | 2002-195984 A | | 7/2002 |
| JP | 2005-106602 | | 4/2005 |
| JP | 2005-106602 A | | 4/2005 |
| JP | 2005147985 A | * | 6/2005 |
| JP | 2005154042 A | * | 6/2005 |
| JP | 2005156419 A | * | 6/2005 |
| WO | WO 93/19380 A1 | | 9/1993 |

OTHER PUBLICATIONS

International Search Report (PCT/ISA/210) dated Feb. 15, 2007.
Chinese Office Action, dated Oct. 9, 2011.

* cited by examiner (A)

(B)

WIRE ROPE FLAW DETECTOR

TECHNICAL FIELD

The present invention relates to a wire rope flaw detector for detecting any damage in a wire rope and disconnection of a component wire thereof (hereinafter collectively referred to as a damaged portion of the wire rope), the wire rope suspending a car of an elevator or the like.

BACKGROUND ART

Conventionally disclosed is a wire rope flaw detector which uses a detection coil to detect leakage magnetic flux generated from a damaged portion, such as disconnection of a component wire, of a wire rope in a magnetic saturated state, whereby the damaged portion of the wire rope is detected (e.g., see patent document 1).

Further, conventionally, in a magnetic flaw detector for wire rope including: an excitation core which has at least two magnetic poles being disposed so as to adjacently face a wire rope and; exciting coils wound around the excitation core; an electric power for supplying a current to the exciting coils; and detection coils disposed between the two magnetic poles to cause polarized magnetic flux to pass through there inside, the polarized magnetic flux having branched off from main magnetic flux passing inside the wire rope through the two magnetic poles, when the wire rope is displaced in its longitudinal direction relative to the excitation core, an electromotive force is excited in the detection coil, whereby mechanical damage on a surface of the wire rope is detected. The magnetic flaw detector characteristically uses an AC electric power as the electric power (e.g., see patent document 2).

[Patent document 1] Japanese Laid-Open Patent Publication No. H09-210968 (Paragraph [0003], FIG. 8, and the like)
[Patent document 2] Japanese Laid-Open Patent Publication No. H11-230945 (claim 1, FIG. 1, and the like)

DISCLOSURE OF THE INVENTION

Problems to be Solved by the Invention

The above conventional wire rope flaw detectors exert sufficient detection performance with respect to damage on a surface and its vicinity of a wire rope, however, they have a problem of failing to detect damage located inside the wire rope.

For example, as described in patent document 1 (Japanese Laid-Open Patent Publication No. H09-210968), in a method of detecting local leakage magnetic flux in the vicinity of the damaged portion of the wire rope, an induced electromotive force generated in the detection coil is proportional to an amount of the leakage magnetic flux. However, in the case of damage inside the wire rope, a large portion of the leakage magnetic flux is shielded by component wires located on and around the surface of the wire rope, and the induced electromotive force generated in the detection coil is small. Thus, it is impossible to obtain a sufficient SN ratio.

Further, as described in patent document 2 (Japanese Laid-Open Patent Publication No. H11-230945), in a method of detecting a difference in permeance between two segments in a wire rope, in the case of an AC-based excitation, the magnetic flux flows so as to concentrate on and around the surface of the wire rope due to a skin effect of the magnetic flux. Therefore, any damage caused inside the wire rope hardly affects a cross-sectional area of a magnetic path, and the difference in the permeance will not be recognized. Thus, it is difficult to detect the damage.

Further, according to the method disclosed in patent document 2 (Japanese Laid-Open Patent Publication No. H11-230945), when a plurality of damaged portions adjacently appear in a wire rope in its longitudinal direction, there is a possibility that the detection accuracy is lowered. For example, suppose a case where damaged portions of a common level have appeared in two predetermined detection segments such that each detection segment has one damaged portion. Since the difference in the permeance between the detection segments is small, an induced voltage caused in the detection coil is low, and thus the SN ratio deteriorates.

An object of the present invention is to solve the above-described problems, and to realize a stable detection accuracy by efficiently capturing local leakage magnetic flux even in the case where damage appears inside a wire rope and consequently the local leakage magnetic flux is attenuated significantly due to a shielding effect of component wires on and around the surface of the wire rope.

Solution to the Problems

A wire rope flaw detector of the present invention includes: a magnetizer forming a main magnetic path in a predetermined segment, in an axial direction, of a wire rope; a magnetic path member disposed within the predetermined segment so as to be magnetically insulated from the magnetizer, and for causing leakage magnetic flux generated from a damaged portion of the wire rope to detour around the wire rope; and a detection coil wound around the magnetic path member for detecting the leakage magnetic flux.

Effect of the Invention

According to the wire rope flaw detector of the present invention, since the magnetic path member is provided, it is possible to improve permeance of the magnetic path of leakage magnetic flux generated in the vicinity of the damaged portion of the wire rope, and also possible to increase an amount of the leakage magnetic flux. Further, since it is possible to extend a length of the magnetic path of the leakage magnetic flux, a disposition area of the detection coil wound around the magnetic path member is increased, and thus the number of turns of the detection coil can be increased. As a result, even when damage occurs inside a wire rope, and the leakage magnetic flux is attenuated due to the shielding effect of component wires on the surface of the wire rope, it is possible to efficiently capture the leakage magnetic flux and also possible to obtain a sufficient SN ratio at the time of flaw detection.

BEST MODE FOR CARRYING OUT THE INVENTION

Hereinafter, preferred embodiments for carrying out the present invention will be described with reference to drawings.

Embodiment 1

Figure 1:
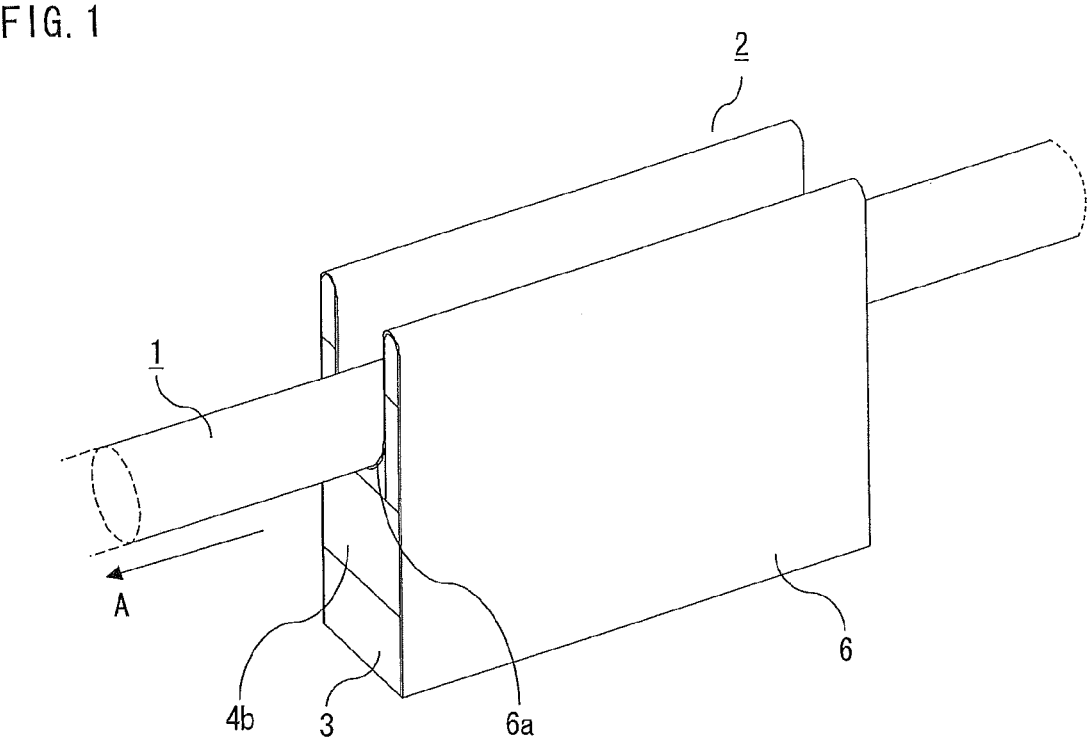
FIG. 1 is a perspective view showing a wire rope flaw detector according to embodiment 1 of the present invention.
Figure 2:
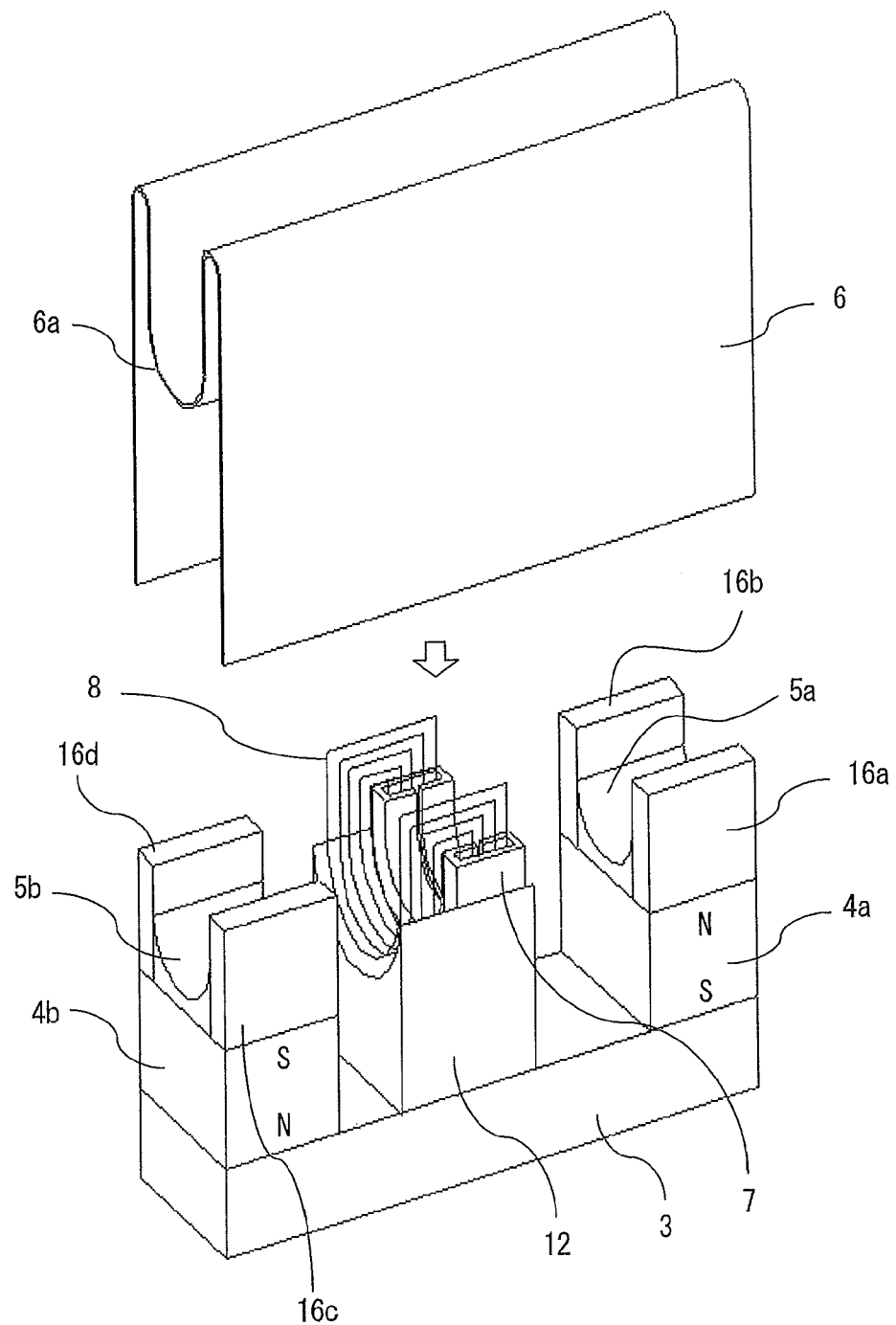
FIG. 2 is a perspective view showing an appearance of the wire rope flaw detector, shown in FIG. 1, in a state where a guide plate thereof is removed.

FIG. 1 is a perspective view showing a wire rope flaw detector according to embodiment 1 of the present invention, and FIG. 2 is a perspective view showing an appearance of the wire rope flaw detector shown in FIG. 1, in a state where a guide plate 6 thereof is removed. In the drawings, a wire rope flaw detector 2 includes the guide plate 6 having a guiding groove 6a of an approximate U-shape so as to allow a wire rope 1 to run through (as indicated by A in the drawing). In the wire rope flaw detector 2 according to the present embodiment, a main magnetic path is formed, by a magnetizer, in a predetermined segment along an axial direction of the running wire rope 1. In addition, the wire rope flaw detector 2 causes leakage magnetic flux generated from a damaged portion of the wire rope 1 to detour through a magnetic path member 7 outside the wire rope 1, whereby the leakage magnetic flux is detected by a detection coil 8 wound around the magnetic path member 7.

The magnetizer of the wire rope flaw detector 2 is designed to generate the main magnetic path in the predetermined segment along the axial direction of the wire rope 1, and includes a back yoke 3 made of a ferromagnetic material such as iron or the like, a pair of excitation permanent magnets 4a and 4b disposed on both ends of the back yoke 3 such that polarities thereof are opposite to each other, and pole pieces 5a and 5b made of a ferromagnetic material and disposed on pole faces of the respective permanent magnets 4a and 4b, the pole faces being the sides opposite to the back yoke 3. Each of the pole pieces 5a and 5b is of an approximate U-shape such that an upper surface thereof fits a curvature of an outer perimeter of the wire rope 1.

Figure 16:
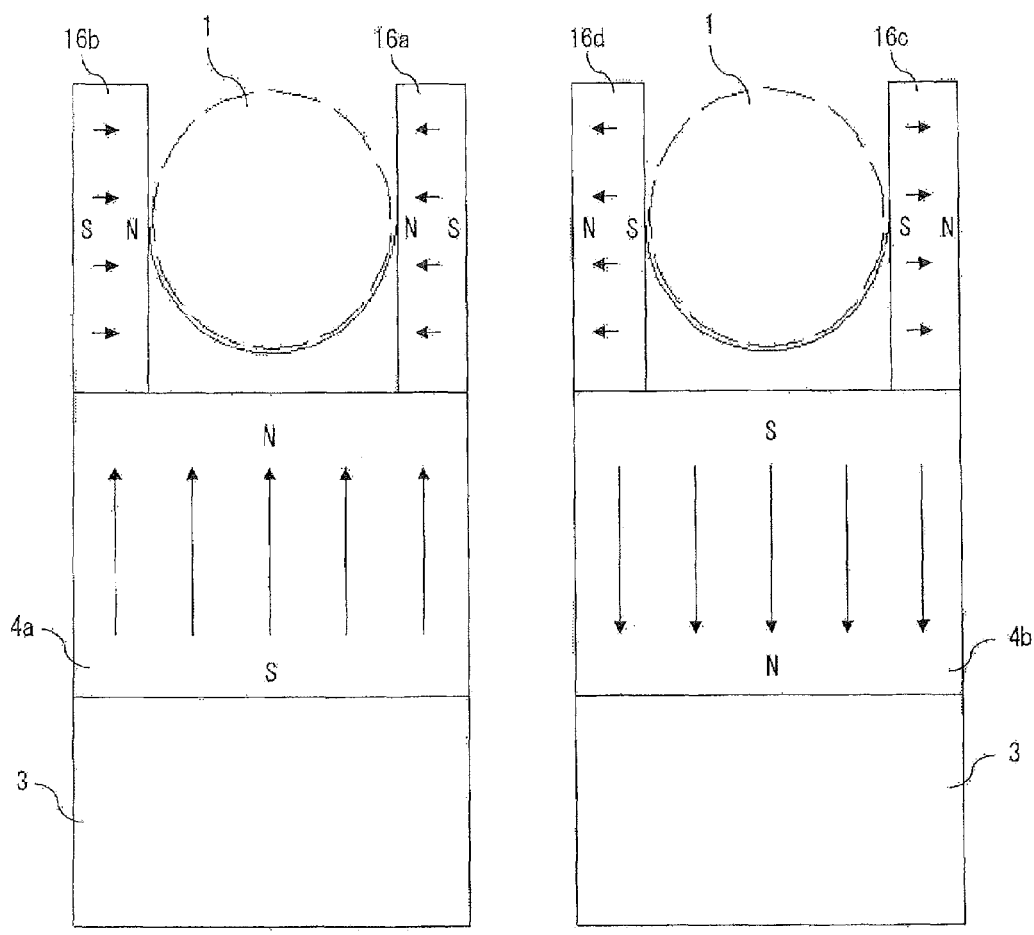
FIG. 16 is a diagram showing a polarity direction of an auxiliary permanent magnet of a magnetizer according to embodiment 1 of the present invention.

Further, auxiliary permanent magnets 16a and 16b are disposed on the permanent magnet 4a, and auxiliary permanent magnets 16c and 16d are disposed on the permanent magnet 4b. As shown in FIG. 16, polarity directions of respective pairs of the auxiliary permanent magnets 16a and 16b, and 16c and 16d are set such that polarities of the respective pairs facing the center of the wire rope 1 are the same as those of the permanent magnets 4a and 4b, respectively. Accordingly, the magnetic flux inside the wire rope 1 is saturated uniformly, which contributes to an increase in local leakage magnetic flux.

The magnetic path member 7 is designed to cause the leakage magnetic flux generated from the damaged portion 10 of the wire rope 1 to detour around the wire rope 1, and is disposed between the pair of permanent magnets 4a and 4b, immediately underneath the guide plate 6. The magnetic path member 7 is made of a ferromagnetic material, and disposed on a supporting base 12, which is made of a non-magnetic material, so as to be magnetically insulated from the main magnetic path composed of the permanent magnets 4a and 4b, the pole pieces 5a and 5b, and the back yoke 3 (excluding the wire rope 1). Further, the magnetic path member 7 has a cross-section of an approximate squared U-shape or of an approximate rounded U-shape in the case where the magnetic path member 7 is cut along a planar surface including a central axis of the wire rope 1, and is situated such that an opening portion of the cross-section faces the wire rope 1. Still further, the magnetic path member 7 is disposed so as to embrace the outer perimeter of the wire rope 1, and has a cross-section of an approximate U-shape, when the magnetic path member 7 is cut along a planar surface perpendicular to the central axis of the wire rope 1. The detection coil 8 to detect the leakage magnetic flux is wound around the magnetic path member 7.

The guide plate 6 is made of a non-magnetic material such as stainless steel or the like, and is disposed so as to substantially adhere to the U-shaped cross-sections of the pole pieces 5a and 5b, and of the magnetic path member 7. The guide plate 6 has a function of protecting the pole pieces 5a and 5b, the magnetic path member 7, and the detection coil 8, and also has a guiding function of allowing the wire rope 1 to run smoothly.

Figure 3:
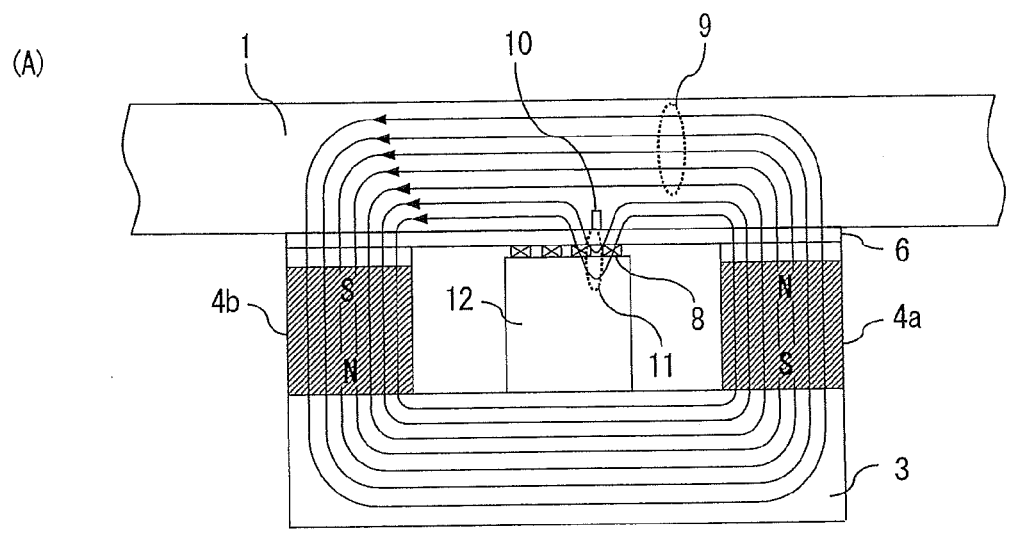
FIG. 3 shows a cross-sectional schematic view of a wire rope flaw detector without a magnetic path member.
Figure 3:
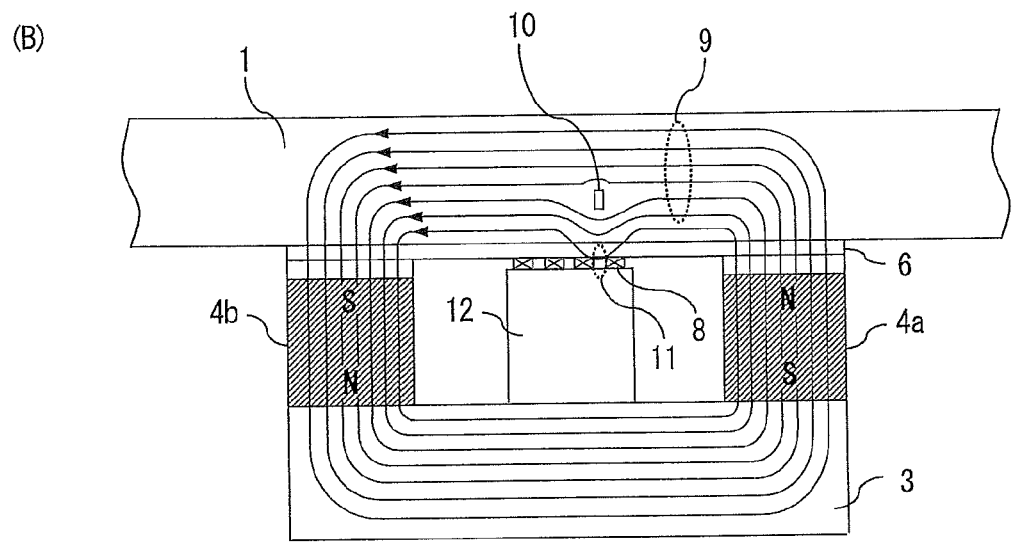

FIG. 3 is a cross-sectional schematic view of the wire rope flaw detector without the magnetic path member 7, and shows a flow of magnetic flux when the damaged portion 10 of the wire rope passes near the detection coil 8. As shown in FIG. 3(A), main magnetic flux 9 generated from the permanent magnet 4a passes through the wire rope 1, the permanent magnet 4b, and the back yoke 3, and then returns to the permanent magnet 4a. Local leakage magnetic flux 11 generated in the vicinity of the damaged portion 10 of the wire rope passes through the non-magnetic guide plate 6, the detection coil 8, and the non-magnetic supporting base 12, and returns to the wire rope 1. Therefore, the permeance of a magnetic path which the local leakage magnetic flux 11 passes along is low. As shown in FIG. 3(B), when the damaged portion 10 of the wire rope is situated inside the wire rope 1, the magnetic flux preferentially passes along component wires at an outer side of the wire rope 1, and thus an amount of the leakage magnetic flux is small.

Figure 4:
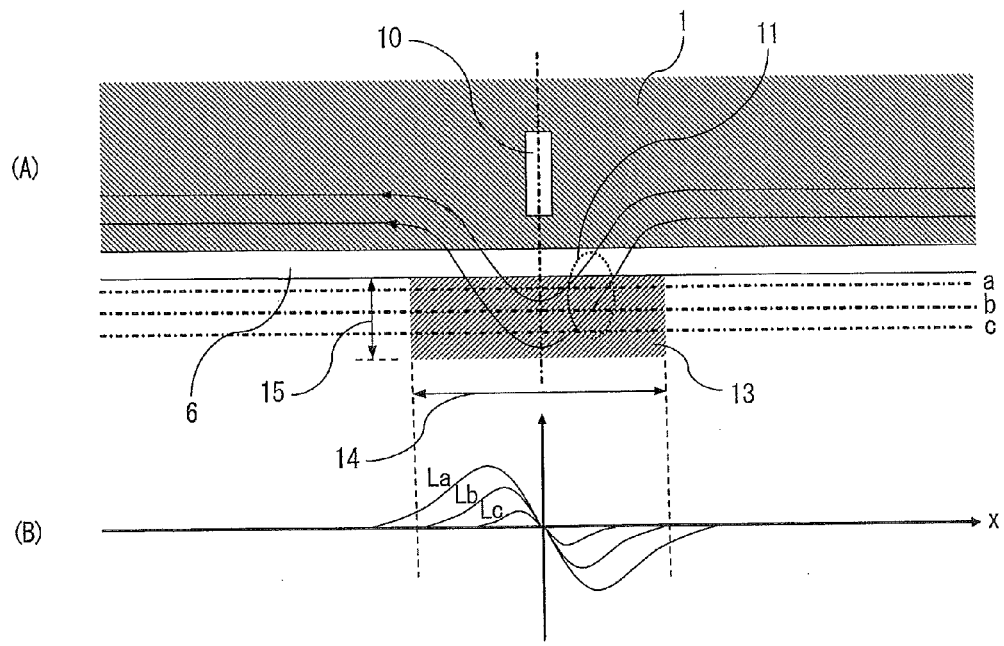
FIG. 4 is an enlarged view showing a flow of local leakage magnetic flux shown in FIG. 3.

FIG. 4 is an enlarged view showing a flow of the local leakage magnetic flux shown in FIG. 3. The local leakage magnetic flux 11 leaking outside the wire rope 1 returns to the wire rope 1 by taking a shortest possible path, and thus an area of the local leakage magnetic flux extending outside the wire rope 1 is small. In a graph shown in FIG. 4(B), curves La, Lb, and Lc respectively show magnetic flux density distributions along chain lines a, b, and c shown in FIG. 4(A), the magnetic flux density being in a radial direction of the wire rope. Suppose the damaged portion 10 of the wire rope is set as a reference point. The farther a position is distant in the wire rope axial direction and in the wire rope radial direction from the damaged portion 10, the smaller the magnetic flux density distribution is. Therefore, a disposition area of the detection coil 8 that effectively generates an induced voltage is generally limited to a shaded area 13 (having an axial direction length 14 and a radial direction length 15) shown in FIG. 4(A). In other words, as will be described later, an increase in the induced voltage will be limited even if the number of turns of the detection coil 8 is increased.

Figure 5:
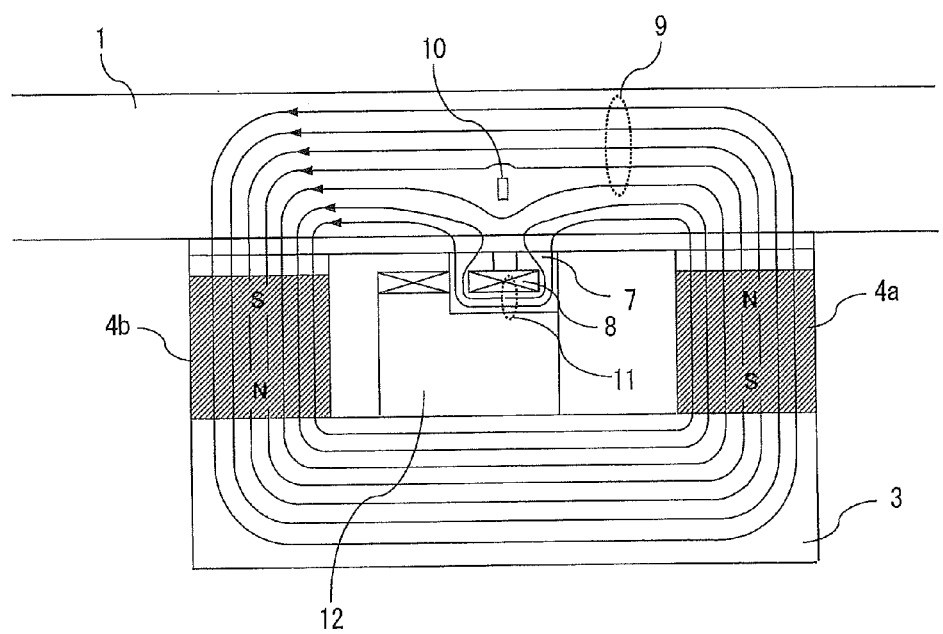
FIG. 5 is a cross-sectional schematic view of the wire rope flaw detector with the magnetic path member according to embodiment 1 of the present invention.
Figure 6:
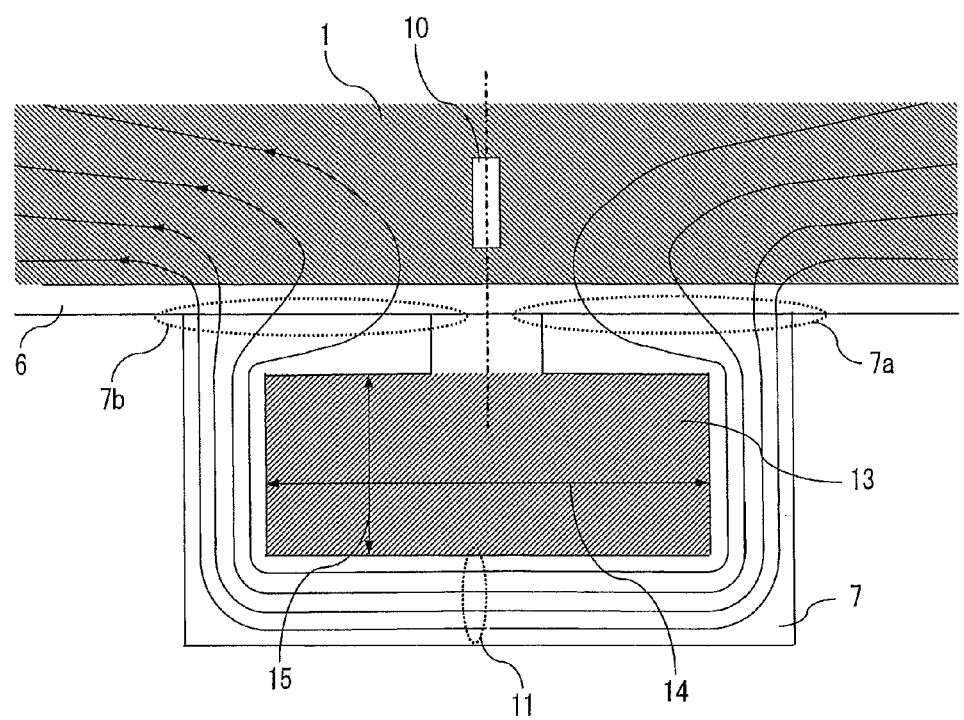
FIG. 6 is an enlarged view showing a flow of local leakage magnetic flux shown in FIG. 5.

FIG. 5 is a cross-sectional schematic view of a wire rope flaw detector with a magnetic path member 7 according to the present embodiment, and FIG. 6 is an enlarged view showing a flow of the local leakage magnetic flux 11 shown in FIG. 5. In the drawings, the local leakage magnetic flux 11 generated in the vicinity of the damaged portion 10 of the wire rope enters from a magnetic flux entrance/exit surface 7a of the magnetic path member 7, passes through the magnetic path member 7 having the cross-section of the approximate U-shape so as to be linked with the detection coil 8, and returns to the wire rope 1 through a magnetic flux entrance/exit surface 7b. Since large portion of the leakage magnetic flux 11 passes through the magnetic path member 8 made of the ferromagnetic material, the permeance of the magnetic path of the leakage magnetic flux 11 is high, and accordingly, an amount of the leakage magnetic flux passing therethrough is increased compared to that passing through a magnetic path made of a non-ferromagnetic material. Further, when the magnetic path of the leakage magnetic flux 11 is caused to detour in the axial direction and in the radial direction of the wire rope, a length of the magnetic path of the leakage magnetic flux 11 can be extended. Accordingly, the axial direction length 14 and the radial direction length 15 of the magnetic path member 7, which constitute the disposition area 13 of the detection coil, can be increased, whereby the number of turns of the detection coil 8 can be increased significantly. As a result, when the damaged portion 10 of the wire rope passes near the detection coil 8, a higher induced voltage can be obtained compared to a case without the magnetic path member 7, and thus it is possible to ensure an SN ratio necessary enough to detect the damaged portion 10 of the wire rope.

Figure 7:
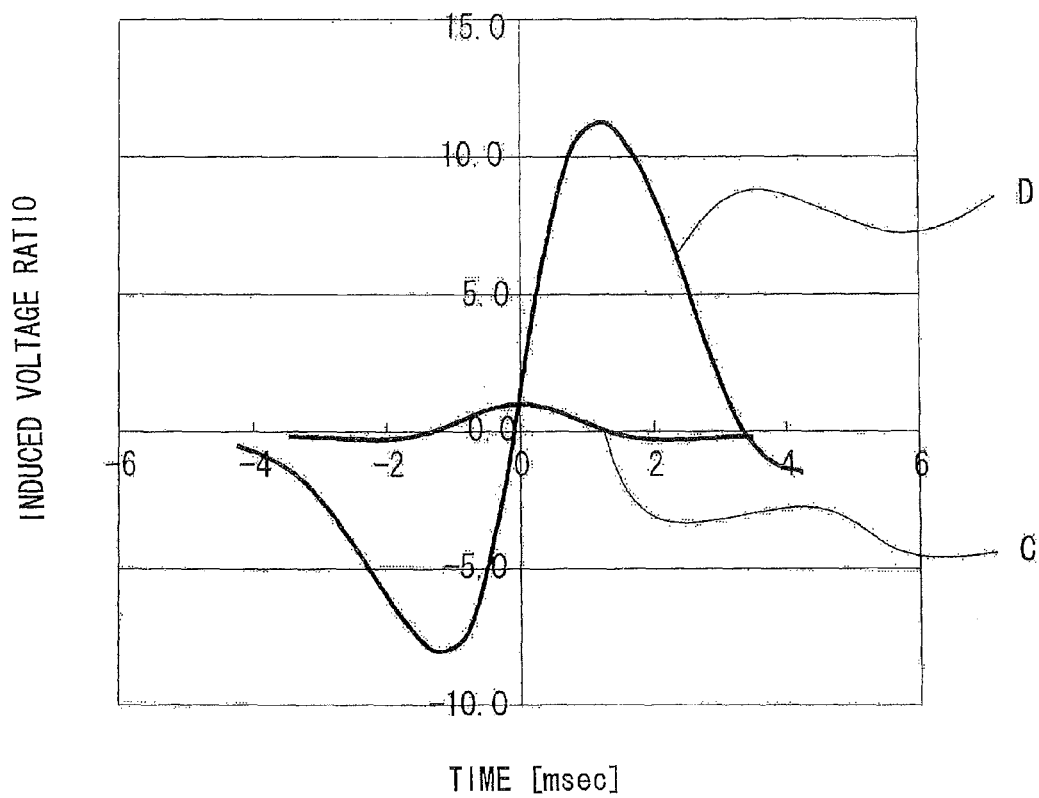
FIG. 7 is a diagram showing induced voltage waveforms when a damaged portion of the wire rope is inspected by using the wire rope flaw detector without the magnetic path member shown in FIG. 3 and by using the wire rope flaw detector with the magnetic path member shown in FIG. 5.

FIG. 7 shows induced voltage waveforms generated at both ends of the detection coil when the damaged portion 10 of the wire rope is inspected by using the wire rope flaw detector without the magnetic path member shown in FIG. 3, and also by using the wire rope flaw detector with the magnetic path member shown in FIG. 5, respectively. Note that both of the above wire rope flaw detectors check a common damaged portion (disconnection part) of a common wire rope. Further, a size of each of the excitation permanent magnets 4a and 4b, a disposition pitch between the same, a size of the back yoke 3, and a running speed of the wire rope 1 applied in both of the wire rope flaw detectors are identical. In the drawing, a waveform C represents an induced voltage waveform inspected by using the wire rope flaw detector without the magnetic path member shown in FIG. 3, whereas a waveform D represents an induced voltage waveform inspected by using the wire rope flaw detector with the magnetic path member 7 shown in FIG. 5. The number of turns of the detection coil in the wire rope flaw detector with the magnetic path member shown in FIG. 5 was five times as many as the number of turns of the detection coil in the wire rope flaw detector without the magnetic path member shown in FIG. 3. In FIG. 7, the horizontal axis indicates time, and time 0 [msec.] represents a time when the damaged portion 10 of the wire rope is aligned with the center of a sensor. The center of the sensor, here, indicates the center of the detection coil 8 in the axial direction in the case of without the magnetic path member shown in FIG. 3, and also indicates the center of the opening portion of the magnetic path member 7 in the case of with the magnetic path member shown in FIG. 5. The vertical axis in FIG. 7 indicates an induced voltage ratio in the case where a peak value of an induced voltage detected by the wire rope flaw detector without the magnetic path member shown in FIG. 3 is set to 1. That is, in FIG. 7, when the peak value of the induced voltage detected by the wire rope flaw detector without the magnetic path member is 1, the peak value of the induced voltage detected by the wire rope flaw detector with the magnetic path member according to the present embodiment is 11.3.

Figure 8:
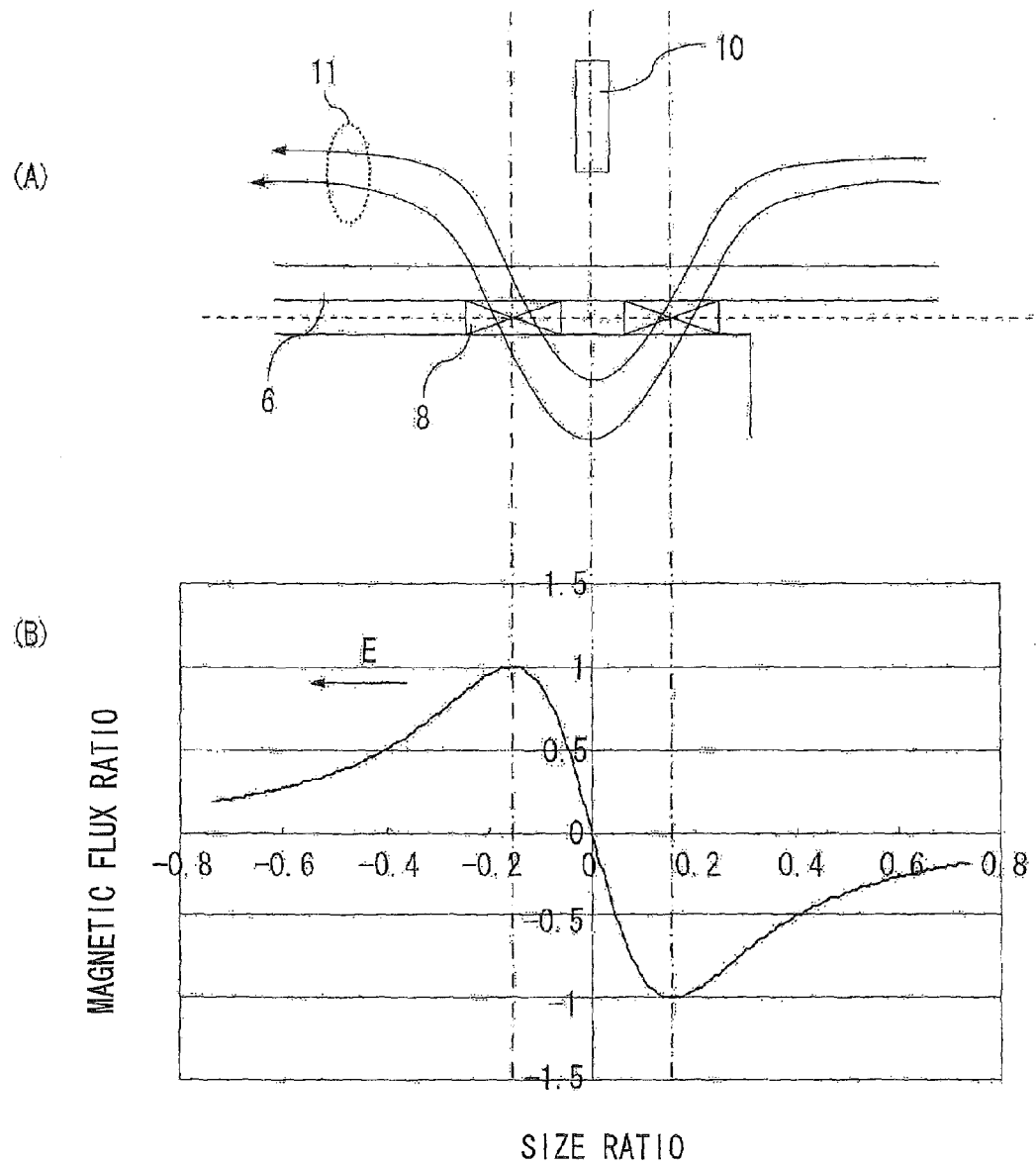
FIG. 8 is a diagram showing a linkage magnetic flux density distribution in the vicinity of a detection coil in the wire rope flaw detector without the magnetic path member shown in FIG. 3.
Figure 9:
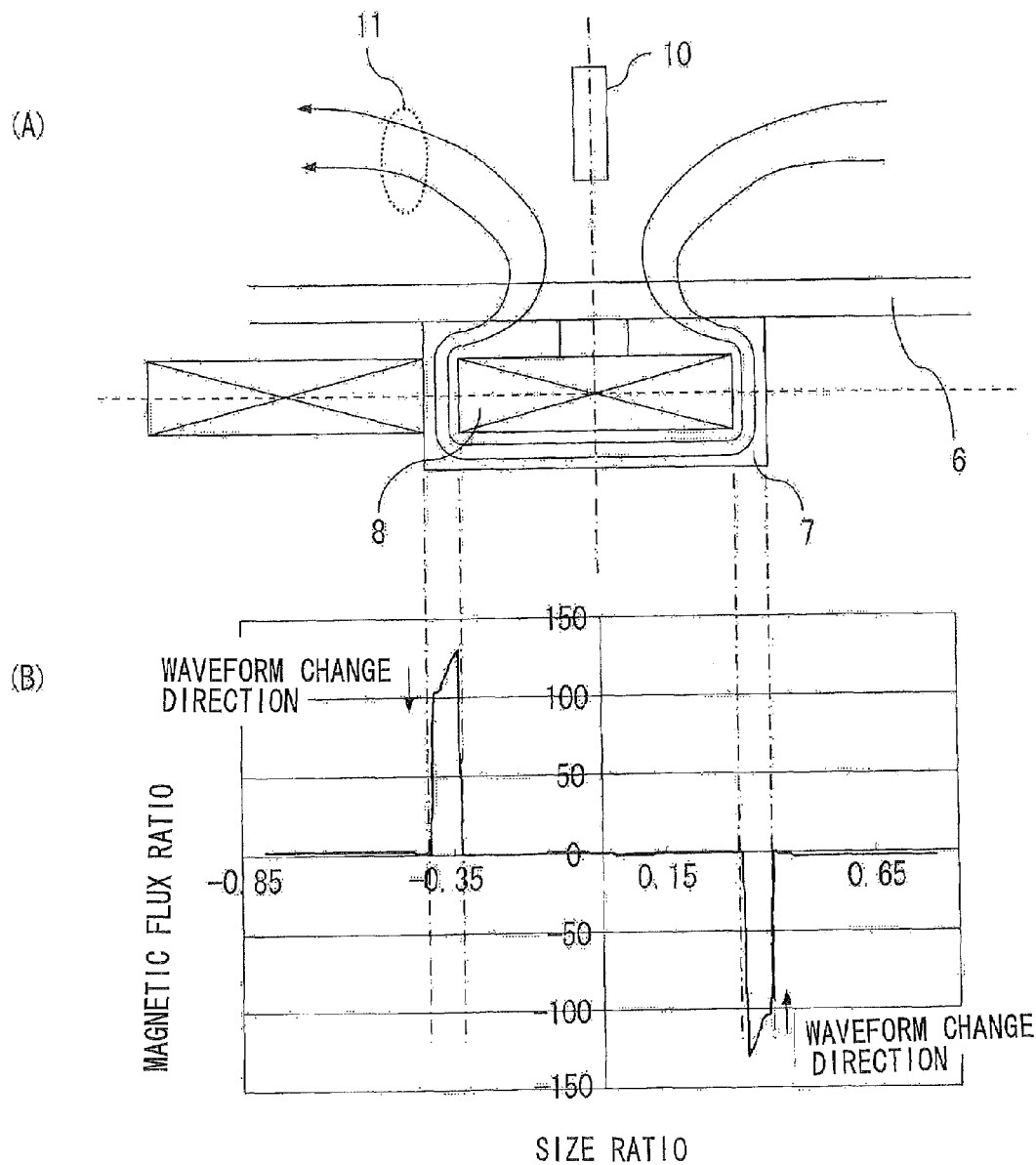
FIG. 9 is a diagram showing a linkage magnetic flux density distribution in the vicinity of a detection coil in the wire rope flaw detector with the magnetic path member shown in FIG. 5.

In FIG. 7, the reason why peaks of the induced voltage waveforms are different between both of the wire rope flaw detectors is described below. FIG. 8 is a diagram showing a linkage magnetic flux density distribution in the vicinity of the detection coil 8 in the wire rope flaw detector without the magnetic path member shown in FIG. 3. When the wire rope 1 shown in FIG. 8(A) runs toward the left side direction of the drawing, the waveform of the magnetic flux density distribution shown in FIG. 8(B) also moves toward the left side direction (direction E). Since the induced voltage generated in the detection coil 8 is proportional to a sum of the magnetic flux densities on respective copper wires constituting the detection coil 8 (so called BLV rule), it is preferable to set an axial direction width of the detection coil 8 to be approximately the same as a wave length of the leakage magnetic flux, and the induced voltage reaches its maximum value when the damaged portion 10 of the wire rope has arrived in the vicinity of the center of the detection coil 8. On the other hand, FIG. 9 is a diagram showing a linkage magnetic flux density distribution in the vicinity of the detection coil 8 in the wire rope flaw detector with the magnetic path member 7 shown in FIG. 5. As shown in FIG. 9, in the case of with the magnetic path member 7, a peak of the magnetic flux density appears at positions where the magnetic path member 7 is disposed, and the magnetic flux density reaches its peak when the damaged portion 10 of the wire rope arrives in the vicinity of the center of the opening portion of the magnetic path member 7. At this stage, the amount of the linkage magnetic flux of the detection coil 8 also reaches its maximum value.

However, according to Faraday's law, the induced voltage is proportional to temporal differentiation of the amount of the linkage magnetic flux, and thus reads 0 at this moment, and the peak of the induced voltage value appears before and after the moment. In each of FIGS. 8 and 9, the vertical axis indicates a magnetic flux density ratio when the peak value of the magnetic flux density in the case of without the magnetic path member is set to 1, and the horizontal axis indicates a size ratio when an outside diameter of the wire rope is set to 1. In addition, each of FIGS. 8(B) and 9(B) shows a magnetic flux density distribution along a dotted line portion in each of FIGS. 8(B) and 9(B), the magnetic flux density being in the radial direction of the wire rope.

Figure 10:
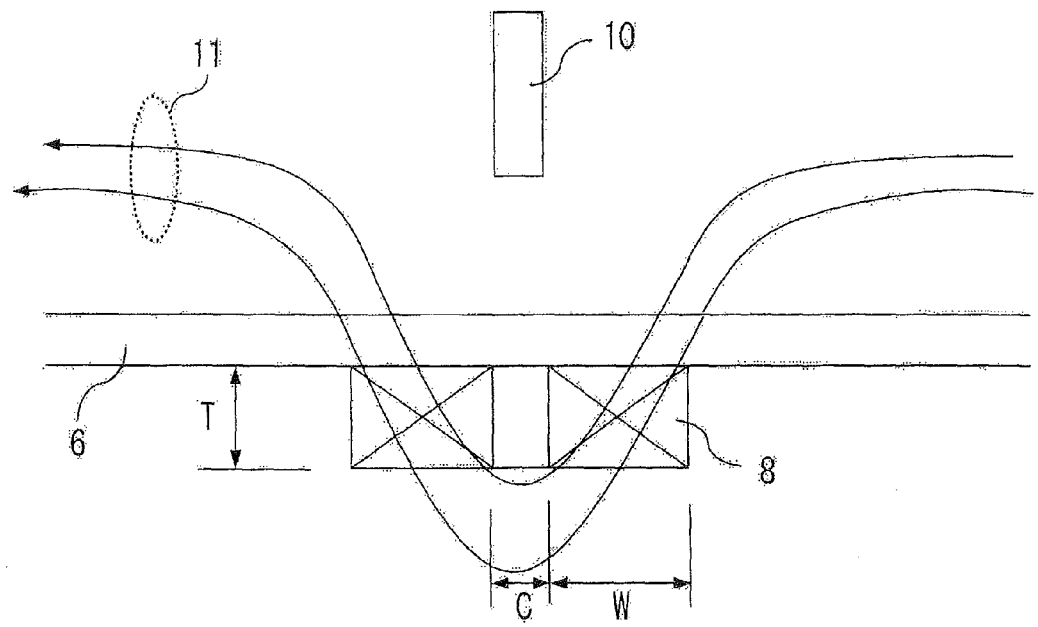
FIG. 10 is a diagram showing the detection coil and its vicinity in the wire rope flaw detector without the magnetic path member.
Figure 11:
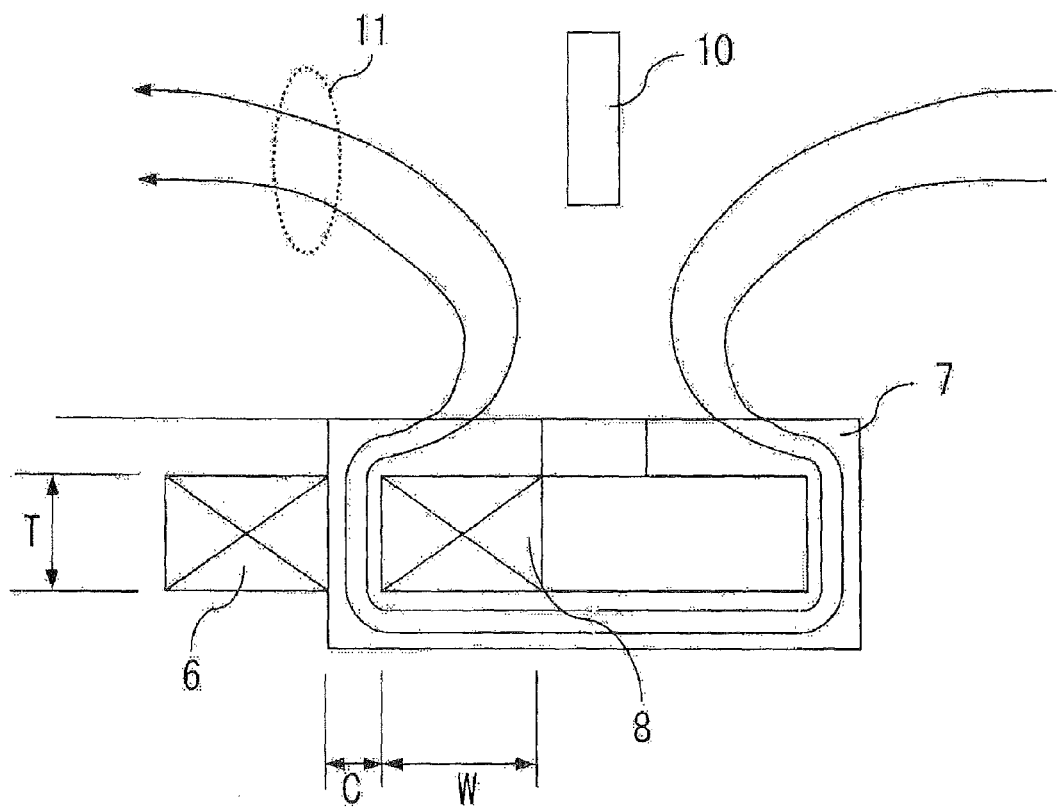
FIG. 11 is a diagram showing the detection coil and its vicinity in the wire rope flaw detector with the magnetic path member.
Figure 12:
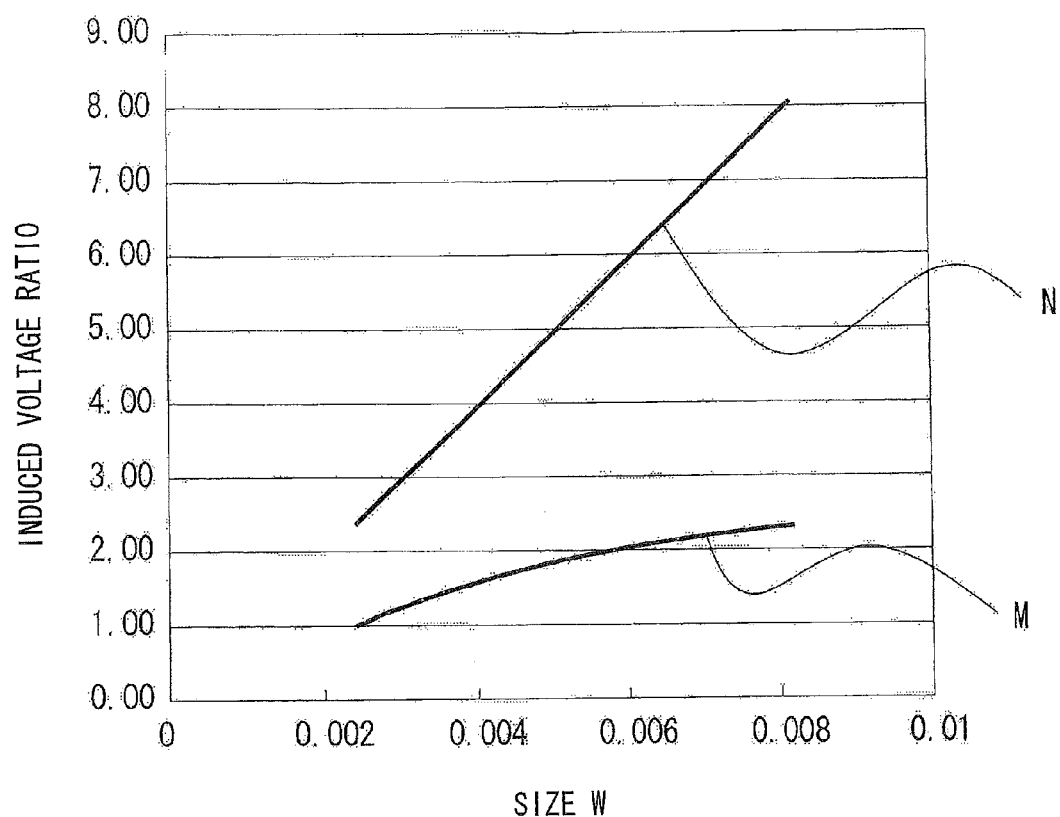
FIG. 12 is a diagram showing peak values of induced voltages when a coil winding width W is increased under a condition where the wire rope flaw detector without the magnetic path member shown in FIG. 10 is used, and also under a condition where the wire rope flaw detector with the magnetic path member shown in FIG. 11 is used.

Next, a relation between a winding width W of the detection coil and the induced voltage will be described. The winding width W of the detection coil is proportional to the number of turns of the detection coil. FIG. 12 shows peak values of the induced voltage when the winding width W of the coil is increased under a condition where the wire rope flaw detector without the magnetic path member shown in FIG. 10 is used, and also under a condition where the wire rope flaw detector with the magnetic path member shown in FIG. 11 is used, respectively. Note that the detection coils 8 having a common winding thickness T and a common core width C are used, and the number of turns per unit area of the cross-section of the detection coils 8 is constant. In FIG. 12, the size of W represented by the horizontal axis indicates its size ratio relative to the outside diameter of the wire rope, and the vertical axis in FIG. 12 indicates the induced voltage ratio when the peak value of the induced voltage detected by using the wire rope flaw detector without the magnetic path member shown in FIG. 10 is set to 1.

In the case of the wire rope flaw detector without the magnetic path member shown in FIG. 10, the induced voltage generated in the respective copper wires constituting the detection coil 8 is proportional to the magnetic flux density in the same area. On the other hand, as shown in FIG. 8, the magnetic flux density decreases at a predetermined distance or more from the damaged portion 10 of the wire rope. Therefore, the induced voltage of coiled copper wires disposed distant from the damaged portion 10 of the wire rope is low. Accordingly, as indicated with a solid line M in FIG. 12, an increment in the induced voltage relative to an increment in the winding width W of the detection coil 8 decreases in accordance with an increase in the winding width W of the coil.

On the other hand, in the case of the wire rope flaw detector with the magnetic path member 7 shown in FIG. 11, the induced voltage generated in the respective copper wires constituting the detection coil 8 is constant regardless of the position of each of the copper wires. Therefore, as indicated with a solid line N shown in FIG. 12, the induced voltage increases in proportional to the winding width W of the detection coil 8.

Figure 13:
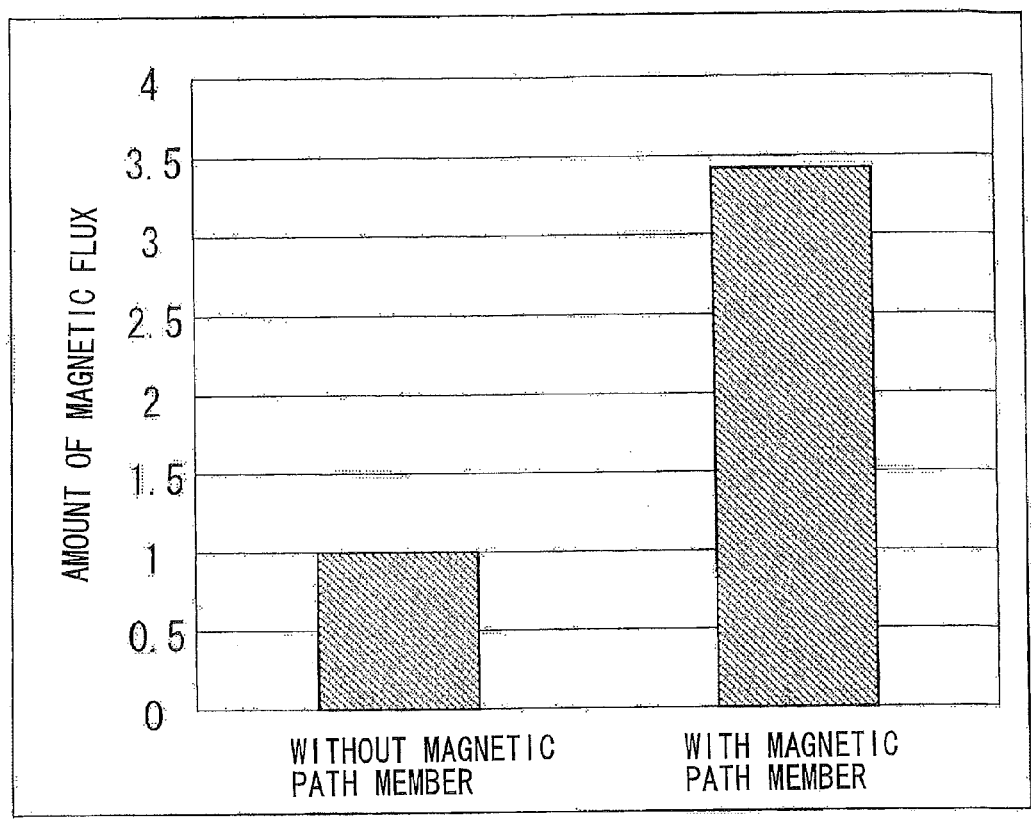
FIG. 13 is a graph showing amounts of leakage magnetic flux in the case where the wire rope flaw detector without the magnetic path member shown in FIG. 10 is used, and also in the case where the wire rope flaw detector with the magnetic path member shown in FIG. 11 is used.

Further, FIG. 13 is a graph showing amounts of the leakage magnetic flux caused by a common damaged portion 10 of the wire rope in the case where the wire rope flaw detector without the magnetic path member shown in FIG. 10 is used, and in the case where the wire rope flaw detector with the magnetic path member shown in FIG. 11 is used, respectively. As shown in FIG. 13, the amount of the leakage magnetic flux caused by the damaged portion 10 of the wire rope is significantly increased when the wire rope flaw detector with the magnetic path member is used compared to when the wire rope flaw detector without the magnetic path member is used. Note that the amounts of the leakage magnetic flux represented by the vertical axis in FIG. 13 are indicated by a ratio therebetween when the amount of the leakage magnetic flux in the case of the wire rope flaw detector without the magnetic path member is set to 1.

As above described, according to the present embodiment, with the magnetic path member 7 causing the leakage magnetic flux generated from the damaged portion 10 of the wire rope to detour around the wire rope 1, it is possible to improve the permeance of the magnetic path of the leakage magnetic flux generated at and around the damaged portion 10 of the wire rope, and accordingly, the amount of the leakage magnetic flux can be increased advantageously. Further, it is possible to extend the length of the magnetic path of the leakage magnetic flux, that is, it is possible to increase a disposition area of the detection coil 8 wound around the magnetic path member 7, and thus the number of turns of the detection coil can be increased. As a result, even if damage occurs inside the wire rope, and the leakage magnetic flux is attenuated due to a shielding effect by component wires on the wire rope surface, the leakage magnetic flux is effectively detected, and an SN ratio sufficient for flaw detection can be obtained.

Since the magnetic path member 7 is magnetically insulated from the main magnetic path composed of the permanent magnets 4a and 4b, the pole pieces 5a and 5b, and the back yoke 3 (excluding the wire rope 1), any portion of magnetic flux does not pass through the magnetic path member 7 other than the leakage magnetic flux 10 that deviates from the wire rope 1 and returns to the wire rope 1. That is, being fundamentally different from above described patent document 2 (Japanese Laid-Open Patent Publication No. H11-230945) which discloses a method of detecting difference in permeance of a wire rope, the present invention can achieve sufficient detection accuracy even in the case of DC energization using a permanent magnet.

Figure 14:
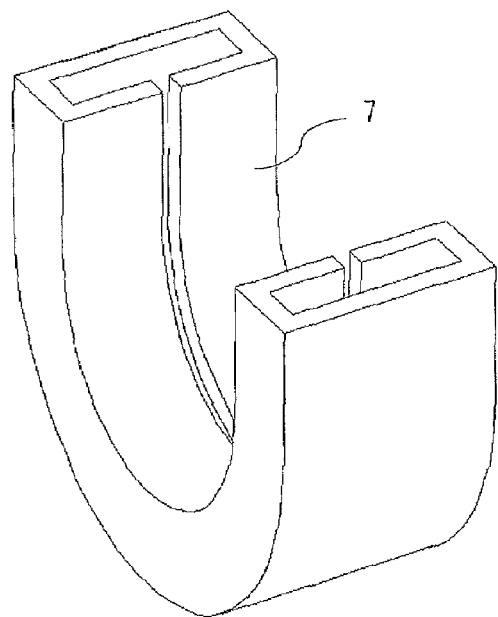
FIG. 14 is a perspective view showing the magnetic path member according to embodiment 1 of the present invention.
Figure 15:
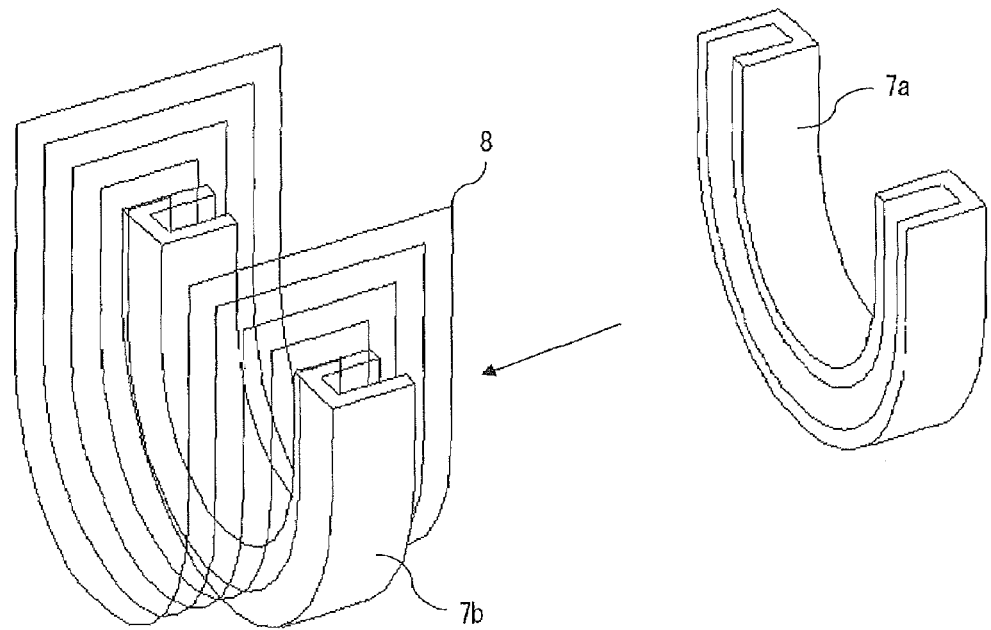
FIG. 15 is a perspective view showing a manner of manufacturing the magnetic path member according to embodiment 1 of the present invention.

FIG. 14 is a perspective view showing the magnetic path member 7 according to the present embodiment. The magnetic path member 7 according to the present embodiment is formed such that a cross-section of an approximate squared U-shape or an approximate rounded U-shape is extruded three-dimensionally to form a U-shape. In other words, the magnetic path member 7 according to the present embodiment is manufactured by linearly extruding a material having a cross-section of an approximate squared U-shape or and an approximate rounded U-shape and then bending the extruded material to form a U-shape. In this case, failure such as cracking or the like is likely to be caused at the time of the U-shape bending, which leads to a quality problem. Therefore, as shown in FIG. 15, a pair of grooved U-shape components 7a and 7b are manufactured, each constituting a half-cut magnetic path member 7. Then, either one of the grooved U-shape components (e.g. 7b) has the detection coil 8 wound around, and joined with the other grooved U-shape component 7b. In this manner, the magnetic path member 7 is composed of at least two components, and the detection coil is wound around one of the components, whereby an operation of winding the detection coil 8 around the magnetic path member 7 is eased, and accordingly, it is possible to improve quality and productivity of the wire rope flaw detector. In this case, with the use of the pair of grooved U-shape components 7a and 7b which constitute halves of the magnetic path member 7 bisected perpendicular to the axial direction, the components of the magnetic path member 7 can be standardized, and consequently the productivity of the wire rope flaw detector is improved.

Figure 17:
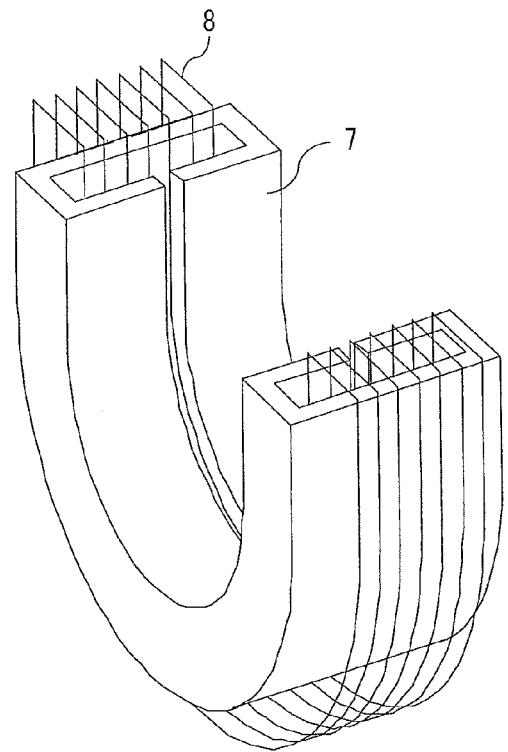
FIG. 17 is a perspective view showing a detection coil in the magnetic path member according to embodiment 1 of the present invention.
Figure 18:
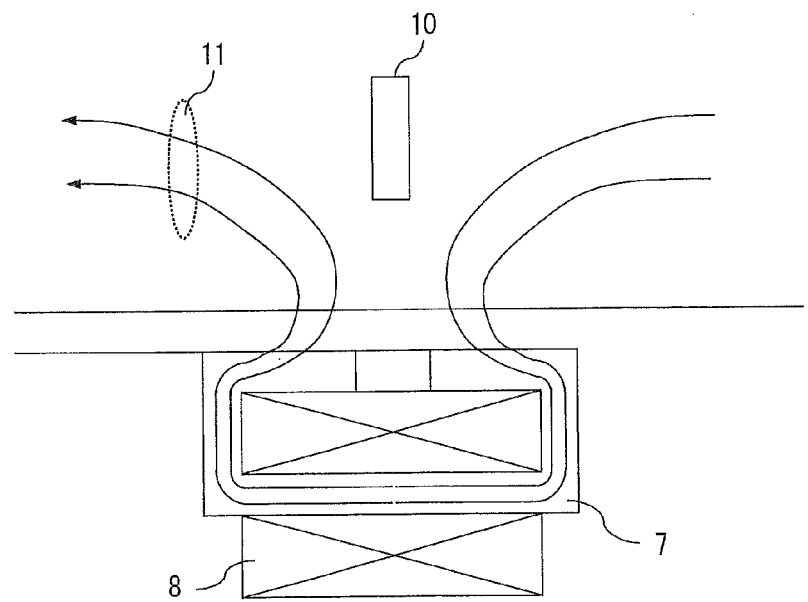
FIG. 18 is an enlarged cross-sectional view showing a detection coil and its vicinity in the magnetic path member shown in FIG. 17.

FIG. 17 is a perspective view showing a manner of winding the detection coil 8 around the magnetic path member 7 according to the present embodiment. FIG. 18 is an enlarged cross-sectional view showing the detection coil and its vicinity shown in FIG. 17. The above-described embodiment has shown an example of the detection coil 8 wound around the magnetic path member 7 in the axial direction of the wire rope 1. However, as shown in FIGS. 17 and 18, it is also possible to obtain a similar effect even when the detection coil 8 is wound around the magnetic path member 7 in the radial direction of the wire rope 1.

Embodiment 2

Figure 19:
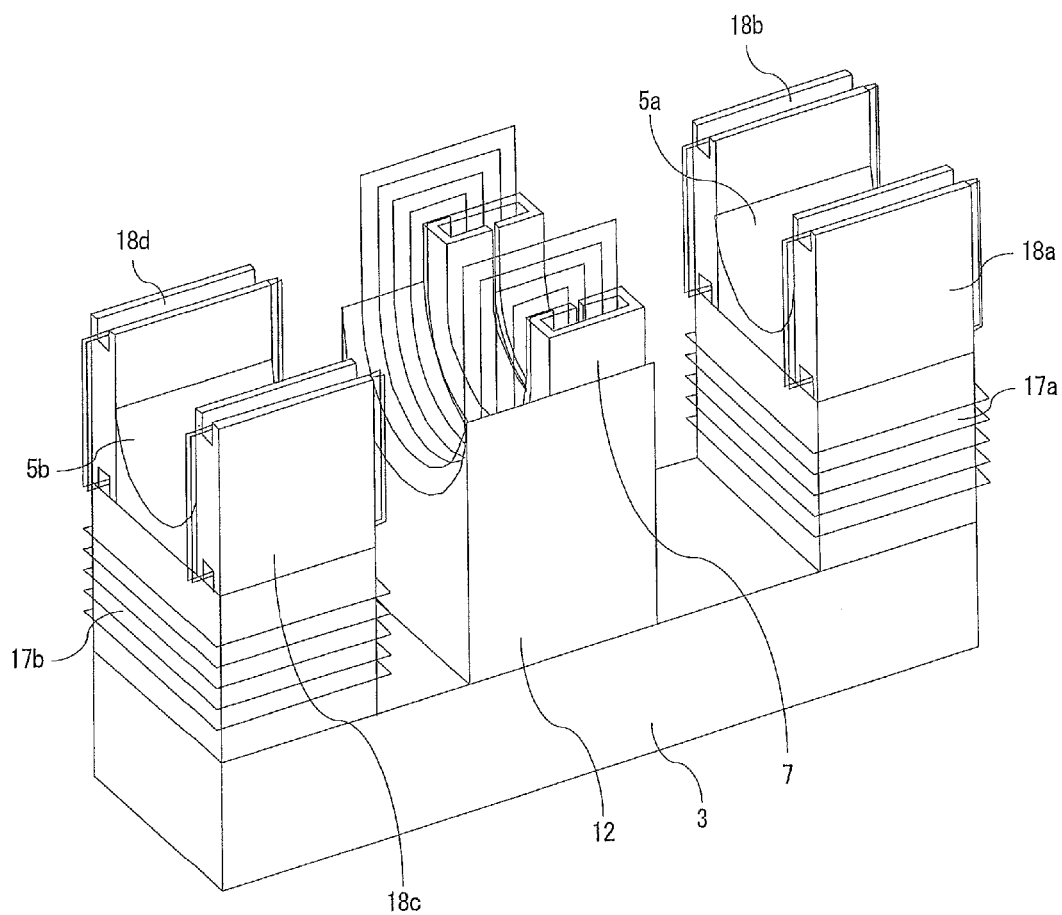
FIG. 19 is a perspective view showing an appearance of a wire rope flaw detector according to embodiment 2 of the present invention, in a state where a guide plate thereof is removed.

FIG. 19 is a perspective view showing an appearance of a wire rope flaw detector according to embodiment 2 of the present invention in a state where a guide plate thereof is removed. In above-described embodiment 1, the magnetizer of the wire rope flaw detector includes the back yoke 3 made of the ferromagnetic material, the pair of excitation permanent magnets 4a and 4b which are disposed on both ends of the back yoke 3, respectively, such that polarities thereof are opposite to each other. In the present embodiment, as shown in FIG. 19, a magnetizer of the wire rope flaw detector includes the back yoke 3 made of the ferromagnetic material, and a pair of excitation electromagnets 17a and 17b which are disposed on both ends of the back yoke 3, respectively, and are excited such that polarities thereof are opposite to each other. In this manner, even when the permanent magnet used in the magnetizer according to embodiment 1 is replaced with the electromagnet, it is possible to obtain the same effect as embodiment 1. In this case, when a current to the excitation electromagnets 17a and 17b is turned off, attractive force is not generated. Accordingly, work efficiency of an inspection worker is improved when the worker attaches/detaches the wire rope flaw detector to/from the wire rope.

In FIG. 19, auxiliary electromagnets 18a and 18b are disposed on the electromagnet 17a, whereas auxiliary electromagnets 18c and 18d are disposed on the electromagnet 17b. Polarity directions of the auxiliary electromagnets 18a and 18b, and 18c and 18d are set such that the polarities of the respective pairs facing the center of the wire rope 1 are the same as those of the electromagnets 17a and 17b, respectively. Accordingly, the magnetic flux inside the wire rope 1 is saturated uniformly, which contributes to an increase in local leakage magnetic flux.

INDUSTRIAL APPLICABILITY

The present invention can be used widely as a wire rope flaw detector for detecting damage in a wire rope or a disconnection of a component wire.

The invention claimed is:

1. A wire rope flaw detector comprising:
a magnetizer forming a main magnetic path in a predetermined segment, in an axial direction, of a wire rope;
a magnetic path member disposed around the predetermined segment so as to be magnetically insulated from the magnetizer, for causing leakage magnetic flux generated from a damaged portion of the wire rope to detour around the wire rope; and
a detection coil wound around the magnetic path member, for detecting the leakage magnetic flux,
wherein the magnetic path member is made of a ferromagnetic material, and has (i) at least two contact surfaces adjoining an outer perimeter of the wire rope directly or through a non-magnetic material interposed therebetween, (ii) a portion other than the contact surfaces, the portion being positioned distant from the outer perimeter of the wire rope as compared to the contact surfaces, and (iii) a space which is positioned between the portion other than the contact surfaces and the wire rope and into which a portion of the detection coil is inserted, and
a length of the space in the axial direction of the wire rope is longer than a length of an opening, in the axial direction of the wire rope, between the at least two contact surfaces.

2. The wire rope flaw detector according to claim 1, wherein the magnetic path member has a cross-section of an approximate squared U-shape or an approximate rounded U-shape when the magnetic path member is cut along a planar surface including a central axis of the wire rope, and is disposed such that an opening portion of the cross-section faces the wire rope.

3. The wire rope flaw detector according to claim 2, wherein the magnetic path member is arranged so as to surround the outer perimeter of the wire rope, and has a cross-section of an approximate U-shape when the magnetic path member is cut along a planar surface perpendicular to a central axis of the wire rope.

4. The wire rope flaw detector according to claim 3, wherein the detection coil is wound around the magnetic path member, which surrounds the outer perimeter of the wire rope, through both ends of the magnetic path member.

5. The wire rope flaw detector according to claim 1, wherein the magnetic path member is composed of two or more components, and one of the components has the detection coil wound therearound.

6. The wire rope flaw detector according to claim 5, wherein the magnetic path member is composed of two components having an identical shape, and one of the components has the detection coil wound there around.

7. The wire rope flaw detector according to claim 1,
wherein the magnetizer comprises:
a back yoke made of a ferromagnetic material; and
a pair of excitation permanent magnets disposed on both ends of the back yoke, respectively, such that polarities thereof are opposite to each other.

8. The wire rope flaw detector according to claim 1,
wherein the magnetizer comprises:
a back yoke made of a ferromagnetic material; and
a pair of excitation electromagnetic disposed on both ends of the back yoke, respectively, and being excited such that polarities thereof are opposite to each other.

* * * * *